United States Patent
Prosise et al.

(10) Patent No.: US 6,312,714 B1
(45) Date of Patent: Nov. 6, 2001

(54) COSMETIC COMPOSITION FOR REJUVENATION OF SKIN WITHOUT SKIN IRRITATION

(75) Inventors: William E. Prosise, Ramsey; Krystyna Plochocka, Scotch Plains, both of NJ (US)

(73) Assignee: ISP Investments Inc., Wilmington, DE (US)

( * ) Notice: Subject to any disclaimer, the term of this patent is extended or adjusted under 35 U.S.C. 154(b) by 0 days.

(21) Appl. No.: 09/166,191

(22) Filed: Oct. 5, 1998

(51) Int. Cl.[7] .............................. A61K 9/70; A61K 2/48; A61K 31/765
(52) U.S. Cl. .................. 424/443; 424/78.2; 514/844
(58) Field of Search ................. 424/70.11, 401, 424/63, 443, 78.2, 78.21, 446; 514/807, 844

(56) References Cited

U.S. PATENT DOCUMENTS 5,037,924 * 8/1991 Tazi et al. ............................. 526/272
5,385,729 * 1/1995 Prencipe et al. .................. 424/70.11
6,046,291 * 4/2000 Zhang et al. .

* cited by examiner

Primary Examiner—Edward J. Webman
(74) Attorney, Agent, or Firm—Walter Katz; William J. Davis; Marilyn J. Maue

(57) ABSTRACT

A cosmetic composition for rejuvenating the appearance of skin with reduced or minimal potential for skin irritation, in the form of a lotion, creme, solution or gel, or applied onto a carrier, includes about 0.5 to 50 wt. % in an aqueous, alcoholic or aqueous-alcoholic solution of a solvent-free, high molecular weight terpolymer of methyl vinyl ether-maleic anhydride-isobutylene, said composition having a pH of 1.5 to 5.

10 Claims, No Drawings

COSMETIC COMPOSITION FOR REJUVENATION OF SKIN WITHOUT SKIN IRRITATION

BACKGROUND OF THE INVENTION

1. Field of the Invention

This invention relates to cosmetic compositions, and, more particularly, to a cosmetic composition for rejuvenating the appearance of skin with substantially no skin irritation.

2. Description of the Prior Art

Cosmetic compositions having an alpha- or beta-hydroxy acid (AHA/BHA) as the active ingredient are well-known in the art. These compositions are useful for treatment of the skin, particularly for anti-aging, improvement in skin tone, reduction of fine line, enhancement of moisture, and development of a smooth skin. Application of such compositions generally results in a younger-looking skin as new cells replace the old. Smith, in Soap/Cosmetics/Chemical Specialties, Sept. 1993, page 54, addressed the question of whether an AHA must be in the acid form to be effective in promoting exfoliation and skin renewal. Various AHA and BHA compounds were examined for their ability to increase cell renewal at different pHs, with similar results observed for all acids tested. As the pH increased, the ability to stimulate cell renewal diminished; in fact, at a pH above 6, very little stimulation of cell turn over was observed with any AHA material. For the acids tested, a maximal stimulation of renewal was observed at a pH of about 3, as shown in Table 1 below.

TABLE 1

Relationship between Cell Renewal, Irritation & pH for Various Acids Tested

| TEST MATERIAL | pH | CELL RENEWAL* | IRRITATION* |
|---|---|---|---|
| 4% Lactic acid | 3 | 35 | 2.8 |
| | 5 | 24 | 2.1 |
| | 7 | 13 | 1.2 |
| 4% Glycolic acid | 3 | 34 | 2.9 |
| | 5 | 23 | 2.1 |
| | 7 | 10 | 1.1 |
| 4% Salicylic acid | 3 | 42 | 3.0 |
| | 5 | 28 | 2.3 |
| | 7 | 12 | 1.2 |
| 5% Citric acid | 3 | 18 | 2.3 |
| | 5 | 14 | 2.1 |
| | 7 | 8 | 1.1 |

*A higher number indicates improved cell renewal/more irritation

Accordingly, to achieve improvement in skin condition, it has been found necessary for the user to tolerate the skin irritation caused by the acid present in the product. Thus, skin irritation is a major concern to formulators of alpha and beta-hydroxy acid-containing products, particularly at acid loading levels which can deliver faster and more effective skin peeling. More irritation, however, is perceived by the user as being a more effective treatment.

Scott and Yu, in EP 671162, have described an amphoteric composition containing AHAs and their esters and salts for topical application for the treatment of cosmetic conditions and dermatological disorders. The inclusion of an amphoteric compound in the composition provided a stable composition having a pH closer to that of skin.

Usumura, in U.S. Pat. No. 5,512,277, described a method of removing keratotic plugs by applying a keratotic plug remover composition onto the skin, and peeling off the composition after the composition was dried, and, particularly, wherein the active ingredient of the composition was a cationic polymer compound such as polymethacryloylethyl trimethylammonium chloride.

Chaudhuri, in U.S. Pat. No. 5,736,128 also described a cosmetic composition for rejuvenating the appearance of skin with reduced or minimal skin irritation which included an anionic copolymer of methyl vinyl ether-maleic acid as the active ingredient in an aqueous, alcoholic or aqueous-alcoholic solution of 0.5 to 25 wt. % of the copolymer at a pH of 1.5 to 5.

U.S. Pat. No. 5,037,924 described the preparation of terpolymers of maleic anhydride, a $C_1$–$C_4$ alkyl vinyl ether and isobutylene, for use as denture adhesives in the form of their mixed salts. These terpolymers were made by precipitation polymerization in the presence of a cosolvent system of ethyl acetate and cyclohexane. The resultant terpolymer had a low molecular weight of about 30,000 to 400,000, and contained residual ethyl acetate and cyclohexane in the terpolymer.

Accordingly, it is an object of this invention to provide a new and improved cosmetic composition for the rejuvenating the appearance of skin which produces excellent skin compatability with substantially no skin irritation, and with the environmental benefit of a residual solvent-free system.

SUMMARY OF THE INVENTION

What is described herein is a cosmetic composition for rejuvenating the appearance of skin with excellent skin compatability, and substantially no skin irritation, in the form of a lotion, creme, solution or gel, or applied onto a carrier, such as woven and non-wovens, in the form of a skin peelable strip, the active ingredient being 0.5 to 50 wt % of a solvent-free, high molecular weight terpolymer of maleic anhydride-methyl vinyl ether-isobutylene, at a pH of 1.5 to 5.

DETAILED DESCRIPTION OF THE INVENTION

The active ingredient of the cosmetic composition of the invention are solvent-free, fine powders of high molecular weight alternating terpolymers of maleic anhydride (MAN), a $C_1$–$C_4$ alkyl vinyl ether (AVE) and isobutylene (IB), having molecular structure of $(A-B)_n$, where A=MAN and B=AVE or IB, and containing preferably about 5 to 25 mole % of isobutylene.

The terpolymers have a molar ratio of maleic anhydride to alkyl vinyl ether to isobutylene of about 0.50:0.45–0.25:0.05–0.25, respectively.

The NMR spectra of these terpolymers show an alternating molecular structure $(A-B)_n$ as described above, where n is such that the terpolymer has a weight average molecular weight (GPC, water pH 9) in excess of about 1,500,000, and a specific viscosity which is $\geq 6$ (1% in DMF, 25° C.).

The powders are made by a solvent-free process which is carried out by charging the alkyl vinyl ether and isobutylene into a reactor at a mole ratio of isobutylene to alkyl vinyl ether which is substantially greater than that desired in the terpolymer, adding a radical initiator, heating the mixture to a reaction temperature of about 50 to 100° C., and feeding molten maleic anhydride over time into the reactor, wherein the mole ratio of maleic anhydride to the total charge of alkyl vinyl ether and isobutylene is not higher than 1:3. The resulting terpolymers obtained herein are odorless and free of the trace amounts of solvents characteristic of other known processes for making such terpolymers.

Preferably the solvent-free polymerization process is carried out using an excess of alkyl vinyl ether and isobutylene as the reaction medium. Such a polymerization reaction is carried out by precharging an AVE/IB mixture of predetermined composition into the reactor, adding a radical initiator, heating to a reaction temperature of about 50° to 100° C., and feeding molten maleic anhydride into the reactor over time.

The mole ratio of MAN to the total of MVE+IB is not higher than 1:3, preferably less than 1:5. Furthermore, the mole ratio of IB to MVE in precharge is made significantly higher than that desired in the terpolymer, preferably about 1:1 IB:MVE for a terpolymer containing 1:2 IB:MVE and about 1:2 IB:MVE for a terpolymer containing 1:4 IB:MVE.

Generally, an additional amount of MVE is added near the end of the polymerization in order to fully react the MAN reactant.

After stripping the remaining MVE and IB, the product is obtained as a fine, odorless powder, without residual solvent.

The invention will now be described with reference to the following examples.

EXAMPLE 1

A 1-liter Parr stainless steel reactor equipped with an agitator, heating mantle and syringe pumps for charging reagents was sparged with nitrogen and charged with 175 g (3.00 mole) of methyl vinyl ether (MVE), 175 g (3.12 mole) of isobutylene (IB) and 0.10 g of lauroyl peroxide. The mole ratio of MVE to IB was 0.96. The charged reactor was heated to 63° C. and the temperature was maintained while molten maleic anhydride (MAN) in an amount of 39.2 g (0.400 mole) was fed into the reactor over a period of 2 hours. The mole ratio of MVE and IB to MAN was 15.3. After holding for 3 hours at 65° C., an additional amount of 50 g (0.86 mole) MVE was added. Then the temperature was raised to 70° C. and maintained for 1 hour. Thereafter the reactor was cooled to room temperature, the pressure was released and the reactor discharged. The reaction product was recovered as a fine, white powder which was dried for 1 hour in a vacuum oven at 65° C. The product was a uniform, fine white powder (62 g), without any unreacted MAN. The specific viscosity (SV), as measured in a 1% DMF solution at 25° C. was 6.94. A $^{13}C$, NMR spectrum showed that the mole ratio of monomers in the terpolymer of MAN:MVE:IB was 0.50:0.34:0.16. The weight average molecular weight (GPC, water, pH 9) of the powder was 2,170,000.

EXAMPLES 2–5

The procedure of Example 1 was followed to provide terpolymers having different ratios of MAN:MVE:IB. The results are shown in Table 1 below.

TABLE 1

| | Example No. | | | |
|---|---|---|---|---|
| Polymer | 2 | 3 | 4 | 5 |
| MVE, g (mol) | 100 (1.72) | 200 (344) | 167 (2.87) | 200 (3.44) |
| IB, g (mol) | 150 (2.67) | 50 (0.89) | 83 (1.49) | 25 (0.44) |
| MAN, g (mol) | 41 (0.418) | 41 (0.418) | 41 (0.418) | 41 (0.418) |
| MVE/IB ratio in the reaction (by mole) | 0.39:0.61 | 0.79:0.11 | 0.66:0.34 | 0.89:0.11 |
| MAN:MVE:IB ratio in polymer (by $^{13}C$ NMR, in mole fractions) | 0.50:0.28:0.21 | 0.50:0.46:0.07 | 0.50:0.40:0.10 | 0.50:0.44:0.05 |
| SV (1%, DMF) | 7.71 | 11.11 | 6.96 | 14.46 |
| Mw (GPC, water, pH 9) | 2,100,000 | 2,101,000 | 2,180,000 | 2,150,000 |

In the skin treatment compositions of this invention, such polymers are employed within a critical solution pH range of 1.5 to 5, preferably between about 2 and about 4.5. Above pH 5, little if any cell renewal or exfoliation is achieved; below pH 1.5, noticeable skin irritation results. If the pH is below 1.5, conventional bases can be used to partially neutralize the composition, i.e. increase the pH as desired.

The present terpolymers are generally employed as a solution, cream, gel or paste, or applied onto a carrier, such as wovens and non-wovens, for example, a plastic or paper backing, in a formulation including a diluent such as water, alcohol, aqueous-alcohol or glycol, or with or on other inactive carrier; which includes between about 0.5 and about 50 wt. % of the terpolymer, preferably 0.75–25 wt. % and more preferably 1 to 15 wt. % of the polymer.

In addition to the diluent, formulations of the polymer may also contain other standard adjuvants such as an emolient, moisturizer, thickener, emulsifier, neutralizer, coloring agent, UV absorber or filter, preservative arid/or gelling agent such as those described below. When employed in the formulation, each of these adjuvants generally are present in an amount of between about 0.1 to 10 wt. % of the formulation.

Emollient

Suitable emollients for use herein include, for example, optionally hydroxy-substituted $C_8$–$C_{50}$ unsaturated fatty acids and esters thereof, $C_1$–$C_{24}$ esters of $C_8$–$C_{30}$ saturated fatty acids such as isopropyl myristate, cetyl palmitate and octyldodecylmyristate (Wickenol 142), beeswax, saturated and unsaturated fatty alcohols such as behenyl alcohol and cetyl alcohol, hydrocarbons such as mineral oils, petrolatum, squalane, fatty sorbitan esters, lanolin and lanolin derivatives, such as lanolin alcohol ethoxylated, hydroxylated and acetylated lanolins, cholesterol and derivatives thereof, animal and vegetable triglycerides such as almond oil, peanut oil, wheat germ oil, linseed oil, jojoba oil, oil of apricot pits, walnuts, palm nuts, pistachio nuts, sesame seeds, rapeseed, cade oil, corn oil, peach pit oil, poppyseed oil, pine oil, castor oil, soybean oil, avocado oil, safflower oil, coconut oil, hazelnut oil, olive oil, grapeseed oil, and sunflower seed oil and $C_1$–$C_{24}$ esters of dimer and trimer acids such as diisopropyl dimerate, diisostearylmalate, diisostearyldimerate and triisostearyltrimerate.

Suitable emollients for use herein include isocetyl alcohol, octyl palmitate, isostearyl neopentanoate and isocetyl stearyl stearate, natural or synthetic oils selected from mineral, vegetable, and animal oils, fats and waxes, fatty acid esters, fatty alcohols, alkylene glycol and polyalkylene glycol ethers and esters, fatty acids and mixtures thereof.

Preferred emollients are selected from hydrocarbons such as isohexadecane, mineral oils, petrolatum, squalane, lanolin alcohol, and stearyl alcohol. These emollients may be used independently or in mixtures and may be present in the composition of the present invention in an amount from about 1% to about 30% by weight, and preferably are present in an amount from about 5% to about 15% by weight of the total composition.

Emulsifier

Suitable emulsifiers for use herein include glyceryl stearate and laureth 23, PEG 20 stearate, and minkamidopropyl dimethyl 2-hydroxyethylammonium chloride.

Moisturizer

Typical moisturizers are glycerin, petrolatum and maleated vegetable oil.

Thickener

The compositions of the invention can also contain a hydrophilic gelling agent at a level from about 0.01% to about 10%, preferably from about 0.02% to about 2%, and especially from about 0.02% to about 0.5%. The gelling agent preferably has a viscosity (1% aqueous solution, 200C., Brookfield RVT) of at least about 4000 mPa.s, more preferably at least about 10,000 mPa.s and especially at least 50,000 mPa.s.

Suitable hydrophilic gelling agents can generally be described as water-soluble or colloidally water-soluble polymers, and include cellulose ethers (e.g. hydroxyethyl cellulose, methyl cellulose, hydroxypropylmethyl cellulose), polyvinylalcohol, polyquaternium-10, guar gum, hydroxypropyl guar gum and xanthan gum.

Among suitable hydrophilic gelling agents are acrylic acid/ethyl acrylate copolymers and the carboxyvinyl polymers sold by the B.F. Goodrich Company under the trademark of Carbopol® resins. These resins consist essentially of a colloidally water-soluble polyalkenyl polyether crosslinked polymer of acrylic acid crosslinked with from 0.75% to 2.00% of a crosslinking agent such as polyallyl sucrose or polyallyl pentaerythritol. Examples include Carbopol 934, Carbopol 940, Carbopol 950, Carbopol 980, Carbopol 951 and Carbopol 981. Carbopol 934 is a water-soluble polymer of acrylic acid crosslinked with about 1% of a polyallyl ether of sucrose having an average of about 5.8 allyl groups for each sucrose molecule. Also suitable for use herein are hydrophobically-modified crosslinked polymers of acrylic acid having amphipathic properties available under the Trade Name Carbopol 1382, Carbopol 1342 and Pemulen TR-1 (CTFA Designation: Acrylates/10–30 Alkyl Acrylate Crosspolymer). A combination of the polyalkenyl polyether cross-linked acrylic acid polymer and the hydrophobically modified crosslinked acrylic acid polymer is also suitable for use herein. Other suitable gelling agents suitable for use herein are oleogels such as trihydroxystearin and aluminum magnesium hydroxy stearate.

Preferred thickeners for use herein include crosslinked maleic anhydride-alkyl methylvinylethers, and copolymers, sold as Stabileze® QM (International Specialty Products (ISP)). Also useful are Carbomer®, natural gums, highly crosslinked polymethacrylate copolymer such as Microsponges® 5647, which take the form of generally spherical particles of crosslinked hydrophobic polymer having a pore size of from about 0.01 to about 0.05 Tm and a surface area of 200–300 m$^2$/g. Again, it is preferably loaded with humectant in the levels described above.

Neutralizer

Neutralizing agents suitable for use in neutralizing acidic group containing hydrophilic gelling agents herein include sodium hydroxide, potassium hydroxide, ammonium hydroxide, monoethanolamine, diethanolamine and triethanolamine, and aminomethyl propanol.

Other Optional Components

Another optional but preferred component of the composition is one or more preservatives. The preservative concentration in the composition, based on the total weight of that composition, is in the range of between about 0.05% and about 1.0% by weight, preferably between abut 0.1% and about 0.4% by weight. Suitable preservatives for use herein include sodium benzoate and propyl paraben, and mixtures thereof.

The composition may also contain additional materials such as, for example, fragrances, fillers such as nylon, sun-screens, electrolytes such as sodium chloride, proteins, antioxidants and chelating agents as appropriate.

Another optional component is one or more ultraviolet absorbing agents. Ultraviolet absorbing agents, often described as sunscreening agents, can be present in a concentration in the range of between about 1% and about 25% by weight, based on the total weight of composition. Preferably, the UV absorbing agents constitute between about 2% and 15% by weight. More preferably, the UV absorbing agents can be present in the composition in a concentration range of between about 4% and about 10% by weight. Of the ultraviolet absorbing agents suitable for use herein, benzophenone-3, benzophenone-4, octyl dimethyl PABA (Padimate O), octyl methoxy cinnamate, octyl salicylate, octocrylene, p-methylbenzylidene camphor, butyl methoxy dibenzoyl methane (Parsol 1789), titanium dioxide, zinc oxide and mixtures thereof are particularly preferred.

The cosmetic compositions of the present invention are useful in the epidermal treatment to achieve cell renewal, skin smoothing, exfoliation, removal of skin blemishes such as freckles, warts, ichthyosis, keratoses, melasma, age spots and other undesirable skin pigmentation. The polymers therein are also useful in the treatment of acne, psoriasis, clogged pores and general improvement of skin tone. The crosslinked polymers described herein additionally provide a moisturizing effect. Many other benefits and uses will become apparent from the above disclosure.

The present polymers provides many advantages for such uses over the non-polymeric acid compounds (AHA or BHA) of the prior art. Specifically, their large molecular size as compared to such compounds prevents penetration through the pores of the skin. Accordingly, skin irritation and toxicity are substantially avoided or minimized during use. Furthermore, polymers containing a carboxylic acid functionality are less acidic than their monomers and thus can be employed in combination with other treating agents, if desired.

Single applications of the skin care compositions containing the instant polymers provides immediate effect in rejuvenating the skin, such as smoothing, moisturizing and toning the skin. Conversely, exfoliation, cell renewal, etc. may require multiple applications of daily or weekly frequency, depending on the skin type of the consumer. Generally, such applications for 0.5 to 6 weeks show a marked effect for skin treatments usually requiring stronger action.

Having generally described the invention, reference is now had to the accompanying examples which illustrate preferred embodiments but which are not to be construed as limiting to the scope of the invention as more broadly set forth above and in the appended claims.

EXAMPLE 1'

Cell Renewal Studies

This example is a comparative cell renewal study of (A) an acid polymer of the invention and (B) a non-polymeric acid compound, against (C) an untreated control, measured by the disappearance of dansyl chloride from the stratum corneum on human skin. Such disappearance of the fluorescent dye is an accepted marker for the transit of cells through the horny epidermal layer, and is therefore a function of the new cell production rate.

In this experiment, the (A) polymer is a maleic acid/methyl vinyl ether/isobutylene terpolymer (Ex. 1), (as an aqueous solution, with a pH of 2.1); (B) is lactic acid, as a 10% aqueous solution; and (C) is dansyl chloride (5-dimethylaminonaphalene-1-sulfonyl chloride), as a 5% petrolatum composition.

Method 50 microliters (μl) of each test sample is applied to spearate sites of the skin of 26 female test subjects (5 a week for 4 weeks). Particularly, Compositions A, B and C are separately tested on the outer, upper arms above the elbow fold of each subject. The test sites are cleansed with 70% isopropyl alcohol. The test sites, 5 cm×5 cm, are initially outlined with gentian violet surgical marker on the first day of testing and a 2 cm space is left between test sites.

In three separate areas, approximately 0.2 g dansyl was placed in a 2 cm×2 cm area in the center of the test site. The control patch site areas are kept dry for 24 hour after which the patches were removed and excess dansyl chloride wiped off. The penetration of the dansyl chloride is confirmed by examination for the presence of fluorescence under ultraviolet illumination using a Wood's light (model SL-3660 Long Wave Ultra Violet, Black Light Eastern Corp., Westbury, Long Island, N.Y.).

On a randomized basis, 50 μl of each test material A and B is evenly spread over a dansyl chloride treated site, and after 24 hour intervals, the results were observed and recorded.

Each of the 26 subjects tested is evaluated for the degree of fluorescent brightness and assigned values of 1 to 5, namely 5=uniform, very bright;

4=uniform moderate brightness

3=faded yet visible fluorescence

2=faded spotty brightness

1=no brightness

The brightness values in following Table 2 represent the total of individual value ratings assigned to each subject in the group of 26 subjects tested. A lower value indicates a higher cell renewal.

The experimental results in Table 2 can establish that a polymer having a carboxylic acid functionality has the same cell renewal efficacy as a non-polymer alpha-hydroxy acid, and both are substantially more effective than the control sample.

TABLE 2

CELL RENEWAL TEST RESULTS
Time in Weeks

| Test Sample | 1 | | | 2 | | | 3 | | | 4 | | |
|---|---|---|---|---|---|---|---|---|---|---|---|---|
| | A | B | C | A | B | C | A | B | C | A | B | C |
| Total Score | 119 | 123 | 128 | 83 | 84 | 99 | 55 | 53 | 64 | 26 | 26 | 48 |

A-an acid polymer of invention
B-a non-polymeric acid compound
C-untreated control

EXAMPLE 2'

Primary Dermal Irritation (PDI) Testing

A comparative test is conducted to determine the extent of reduction of irritation during use of the polymers of the invention (Test Samples A) vs. alpha- and beta-hydroxy acids (Test Samples B), below.

In this study, a panel of 12 volunteers is selected from people who previously reported moderate stinging following application of a standard lactic acid solution. These people are asked to report their reactions to standard Test Sample B aqueous solutions of lactic acid, glycolic acid, salicyclic acid and citric acid, and also to aqueous and undiluted Test Sample A solutions of poly(methylvinyl ether/maleic acid/isobutylene, (Ex. 1), poly(vinylpyrrolidone/acrylic acid, and polyacrylic acid at a pH of about 2.5. These materials are randomly applied with a cotton-tipped applicator to either the left or right naso-labial fold. Subjective reactions are reported on a PDI scale of 0–3, with 0 being no irritation, 10 seconds, 2½ and 5 minutes after application. The results are given in Table 3 below.

TABLE 3

| Test Samples | Materials tested | pH | Use Level | PDI |
|---|---|---|---|---|
| A | Poly(methyl vinyl ) ether/maleic acid)/ isobutylene (Ex. 1) | 2.8 | 10% aq. sol. | 0 |
| | Poly(vinyl-pyrrolidone/) acrylic acid) 75:25 (ACRYLIDONE ® 1001) (10% in ETOH/H$_2$O 1:1) | 3.1 | undiluted | 0.63 |
| | Polyacrylic acid (10% solution) | 2.5 | undiluted | 0 |
| B | Lactic acid | 3 | 4% aq. sol. | 2.8 |
| | Glycolic acid | 3 | 4% aq. sol. | 2.9 |
| | Salicylic acid | 3 | 4% aq. sol. | 3.0 |
| | Citric acid | 3 | 5% aq. sol. | 2.3 |

TABLE 3

Composition of Invention

| | % by Wt. | |
|---|---|---|
| | Suitable | Preferred |
| Essential Components | | |
| Polymer of Invention | 0.5 to 25 | 1 to 10 |
| Water | 20 to 95 | 50–90 |

TABLE 3-continued

Composition of Invention

| | % by Wt. | |
|---|---|---|
| | Suitable | Preferred |
| Optional Components | | |
| Emollient | 0 to 30 | 1–20 |
| Moisturizer | 0 to 30 | 1–20 |
| Emulsifier | 0 to 20 | 0.5–15 |
| Thickener | 0 to 30 | 0.5–20 |
| Neutralizer | 0 to 5 | 0.1–2 |
| Preservative | 0 to 1.0 | 0.1–0.5 |
| Sunscreen | 0 to 25 | 4–10 |
| pH | 1.5 to 5.0 | 3–4 |

The invention will now be illustrated by the following examples.

EXAMPLE 3'

A skin creme composition containing poly (methylvinylether/maleic acid/isobutylene) was formulated as follows:

| Base Composition | % by Wt. | | |
|---|---|---|---|
| Water Phase | | | |
| H₂O, deionized | QS | QS | QS |
| Stabileze ® QM (ISP) | 1.5 | 2.0 | 2.0 |
| Plasdone ® K 29/32 (ISP) | 1.0 | 1.0 | — |
| Suttocide ® A (Sutton) | 0.5 | 0.5 | 0.5 |
| Polymer of Invention | | | |
| Poly(methylvinylether/ maleic acid/isobutylene) (Ex. 1) | 5.0 | 5.0 | 5.0 |
| Neutralizer | | | |
| Sodium Hydroxide (25% Aqueous solution) Adjust pH to 4.0 | qs | qs | qs |
| Oil Phase | | | |
| Ceraphyl ® 65 (ISP) | 1.0 | 1.0 | 1.0 |
| Ceraphyl ® ICA (ISP) | 5.0 | 5.0 | 5.0 |
| Ceraphyl ® 368 (ISP) | 5.0 | 5.0 | 5.0 |
| Ceraphyl ® 791 (ISP) | 7.0 | 7.0 | 7.0 |
| Cerasynt ® 945 (ISP) | 5.0 | 5.0 | 5.0 |
| Cerasynt ® 840 (ISP) | 2.0 | 2.0 | 2.0 |
| Preservative | | | |
| Germaben ® II (Sutton) | 1.0 | 1.0 | 1.0 |

Procedure
(1) Add Plasdone® K 29/32 to water-mix until totally dissolved.
(2) Add Stabileze® QM to water mix, then heat to 750C. and mix until hydrolyzed.
(3) Cool to 600C. add Suttocide® A.
(4) Add terpolymer/NaOH.
(5) Add oil phase at 600 mix for 10 minutes.
(6) Homogenize 15 minutes.
(7) Cool to 400, add preservative.
(8) Adjust for water loss.

EXAMPLE 4'

A skin creme composition containing polyacrylic acid was prepared as follows.

| Water Phase Composition | |
|---|---|
| H₂O, deionized | qs |
| Stabileze ® QM | 2.0 |
| Polyacrylic acid | 2.5 |
| NaOH (25% aq) to adjust pH to 4.0 | qs |
| Oil Phase | |
| Ceraphyl ® 65 | 1.0 |
| Ceraphyl ® ICA | 5.0 |
| Ceraphyl ® 368 | 5.0 |
| Ceraphyl ® 791 | 7.0 |
| Cerasynt ® 945 | 5.0 |
| Cerasynt ® 840 | 2.0 |
| Germaben ® II | 1.0 |

Procedure
Add polyacrylic acid to water—mix until completely dissolved; then add Stabileze® QM mix well, heat to 750C., forming a smooth, white mixture; cool to 600C.; add Suttocide® A, keeping temperature at 600C.; add oil phase at 600C.; mix for 10 minutes, homogenize 15 minutes, a thin water-like consistency; cool; add the neutralizer to bring pH to 4.0.

EXAMPLE 5'

A skin care facial toner composition containing the terpoymer of the invention was prepared as described in Example 4 above. The compositions included:

| | % W/W |
|---|---|
| Water, DI | 68.64 |
| Terpolymer (Ex. 1) | 4.0 |
| Ceraphyl 60 | 0.5 |
| Glycerine | 5.0 |
| Non-alcoholic witch hazel | 10.0 |
| Tetrasodium EDTA | 0.05 |
| FD & C Red (1.0% aq. sol.) | 0.02 |
| Germaben II | 0.5 |
| NaOH (10% solution)* | qs |

*Adjust pH

EXAMPLE 6'

An after-sun gel composition containing the terpolymer of Ex. 2 was prepared as follows:

| | % W/W |
|---|---|
| Ingredients Water Phase | |
| Water, deionized | qs |
| Propylene glycol and diazolidinyl urea and methylparaben and propylparaben | 1.00 |
| Polymethacrylic acid | 2.00 |
| P(VP-VA) S 630 | 1.00 |
| Premix | 3.80 |
| Water deionized | 3.0 |
| Terpolymer of Ex. 2 | 6.0 |
| Triethanolamine, 99% adjust pH to 4.0 | qs |
| OIL PHASE | q.s. |
| Maleated soybean oil | 27.0 |
| Isocetyl alcohol | 28.0 |
| Dioctyl malate | 28.5 |

-continued

|  | % W/W |
|---|---|
| Alpha-bisabolol | 4.5 |
| Microcrystalline wax | 5.0 |
| Alpha tocopheryl acetate | 3.5 |

Procedure (1) At room temperature add ingredients of water phase in order listed. Mix until completely uniform between additions. Do not aerate.
(2) Add premix to water phase slowly. Do not aerate.
(3) Add polymer of invention.
(4) At 850C. add ingredients of the oil phase to separate vessel in order listed. Mix until uniform between additions.
(5) While in liquid form, add oil phase to water phase in desired design.

EXAMPLE 7'

Facial Exfoliating Cream

| INGREDIENTS | % W/W |
|---|---|
| Oil Phase | |
| Cetyl lactate | 0.25 |
| Tridecyl neopentanoate | 10.00 |
| Shea Butter | 1.00 |
| Cocamide MEA | 5.00 |
| Glycol stearate and other ingredients | 3.00 |
| Mica and bismuth oxychloride and Chromium hydroxide | 2.25 |
| Water Phase | |
| Deionized water | qs |
| Hydroxyethylcellulose | 2.00 |
| Ganex ® P 904 | 2.00 |
| Terpolymer of Ex. 2 | 3.00 |
| Premix | |
| Glycerin | 3.00 |
| Propylparaben | 0.20 |
| Methylparaben | 0.20 |
| Maleated soybean oil | 3.00 |
| Phenoxyethanol | 0.50 |
| Squalane | 0.05 |
| Fragrance | 0.25 |
| Jojoba wax (40/60) | 3.00 |

Procedure (1) Heat water to 850C.
(2) Disperse hydroxyethylcellulose in water until clear and uniform. Add Ganex® P 904 followed by terpolymer.
(3) Add paraben premix.
(4) Heat oil phase to 850C. and mix until uniform.
(5) Add oil phase to water phase. Mix well with sweep blade.
(6) Homogenize.

(7) Cool to 400C. while mixing.
(8) Add remaining ingredients in order listed, mixing well between additions.

EXAMPLE 8'

Eye Cream

| INGREDIENTS | % W/W |
|---|---|
| Oil Phase A | |
| Octyl methoxycinnamate | 2.00 |
| Cetyl lactate | 4.00 |
| Petrolatum, white | 3.00 |
| Octyldodecyl stearoyl stearate | 3.00 |
| Glycol and other ingredients | 6.00 |
| Isocetyl alcohol | 2.00 |
| PEG-20 stearate | 4.00 |
| Cetyl alcohol | 3.00 |
| Terpolymer of Ex. 2 | 3.00 |
| Water Phase | |
| Carbomer 980 | 1.00 |
| Poly(maleic acid) | 2.00 |
| Deionized Water | 58.18 |
| Premix | |
| Propylene Glycol | 3.00 |
| Methylparaben | 0.20 |
| Propylparaben | 0.20 |
| Premix | |
| Triethanolamine 99% | Adjust pH to 4.0 |
| Deionized water | 3.00 |
| Premix | |
| Imidazolidinyl urea | 0.30 |
| Deionized water | 3.00 |
| Maleated soybean oil | 3.00 |
| Allantoin | 1.00 |
| Acetamide mea and collagen amino acids and silk amino acids and hydrolyzed elastin | 0.10 |
| Propylene glycol and kiwi fruit extract | 0.25 |
| Lecithin and superoxide dismutase | 0.25 |
| Aloe vera gel (10X concentration | 0.02 |

Procedure (1) Completely disperse Carbomer in water with heat to 850C. Add poly(maleic acid).
(2) Add propylene glycol premix. Then TEA premix.
(3) Heat oil phase to 850C. Mix until uniform.
(4) Add oil phase to water phase. Mix until uniform with a sweep blade.
(5) Homogenize.
(6) Cool to 450C. while mixing with a sweep blade.
(7) Add imidazolidinyl urea premix. Mix until uniform.
(8) Add remaining ingredients in order listed. Mix well.

Note: cream will become lustrous overnight.

EXAMPLE 9'

Body Lotion

| INGREDIENTS | % W/W |
|---|---|
| Phase A | |
| Water deionized | q.s. |
| PVM/MA decadiene crosspolymer | 0.5 |
| Terpolymer of Ex. 2 | 2.5 |
| Phase B | |
| Sodium hydroxymethylglycinate | 0.4 |
| Phase C | |
| Isocetyl stearoyl stearate | 10.0 |
| Glyceryl stearate | 5.0 |
| Tridecyl neopentanoate | 10.0 |
| PEG-20 stearate | 2.0 |
| Phase D | |
| Maleated soybean oil | 3.0 |
| | 100.0% |

Procedure (1) Heat Phase A with agitation to 8500., mix until uniform (40–45 minutes).
(2) Lower temperature to 600C. Add Phase B.
(3) Heat Phase C to 850C., mix until uniform.
(4) Reduce heat to 600C.
(5) Add Phase C to Phase A/B while homogenizing for approximately 5–10 minutes, being careful not to aerate the batch.
(6) Remove. Add Phase D using a sweep blade.
(7) Sweep to 250C.
(8) Adjust pH to 3.5 with NaOH (10% aq.)

EXAMPLE 10'

Sunscreen Lotion with Escalol ® Sunscreens

| INGREDIENTS | % W/W |
|---|---|
| Phase A | |
| Water, deionized | 50.40 |
| Xanthan Gum | 1.00 |
| Propylene glycol | 6.00 |
| PVP K-30 | 1.00 |
| Terpolymer of Ex. 2 | 2–8 |
| Phase B | |
| Glyceryl stearate and laureth-23 | 6.00 |
| PEG-20 stearate | 3.00 |
| Cetyl lactate | 3.00 |
| $C_{12}$–$C_{15}$ alkyl lactate | 1.00 |
| Myristyl myristate | 4.00 |
| Octyl methoxycinnamate or octyl dimethyl PABA | 7.50 |
| Benzophenone-3 | 3.00 |
| Octyl Salicylate | 3.00 |
| Premix | |
| Titanium dioxide and aluminum hydroxide and stearic acid | 5.00 |
| Isocetyl stearoyl stearate | 3.00 |
| Maleated soybean oil | 3.00 |
| Phase C | |
| Diazolidinyl urea and propylene glycol and methylparaben and propylparaben | 1.00 |
| Phase D | |
| Fragrance (Pina Colada AL-60) | 0.10 |

Procedure (1) Prepare premix with roller mill.
(2) Disperse the gum cold with high speed mixing, then add propylene glycol and lactic acid. Heat to 750C.
(3) Heat Phase B to 800C. add premix.
(4) Add Phase B to Phase A, mix for approximately 10 minutes.
(5) Place under homogenizer and mix for approximately 15 minutes.
(6) Remove. Mix to 400C. using sweep blade.
(7) Add Phase C, then add Phase D.
(8) Mix to 250C. using sweep blade.

EXAMPLE 11'

Body Lotion

| INGREDIENTS | % W/W |
|---|---|
| Oil Phase | |
| Glyceryl stearate | 5.00 |
| Octyl methoxycinnamate | 7.50 |
| Benzophenone-3 | 3.00 |
| Octyl salicylate | 3.00 |
| Tridecyl neopentanoate | 10.00 |
| PEG-20 stearate | 2.00 |
| Terpolymer of Ex. 2 | 5.00 |
| Water Phase | |
| Deionized water | 56.00 |
| Carbomer ® 951 | 2.00 |
| Polyacrylic acid | 2–10 |
| Preservative Premix | 3.40 |
| Propylene glycol | 3.0 |
| Methylparaben | 0.2 |
| Propylparaben | 0.2 |
| Triethanolamine Premix | 3.30 |
| Triethanolamine, 99% | qs to pH 4.0 |
| Deionized water | 3.0 |
| Imidazolidinyl urea premix | 3.30 |
| Imidazolidinyl urea | 0.3 |
| Deionized water | 3.0 |
| Lecithin and superoxide dismutase | 0.05 |
| Maleated soybean oil | 3.00 |
| Chamomile extract | 0.05 |
| Fragrance | 0.20 |

Procedure (1) Mix Carbomer® and deionized water at 850C. until uniform. Add polyacrylic acid and mix until uniform.
(2) Add preservative premix.
(3) Slowly add triethanolamine premix.
(4) In separate vessel mix oil phase until uniform at 850C.
(5) Add oil phase to water phase slowly. Mix at 850C. until uniform.

(6) Homogenize.
(7) Mix while cooling to 450C.
(8) Add imidazolidinyl urea premix.
(9) Add remaining ingredients one at a time, stirring well between additions.

EXAMPLE 12'

| Aqueous Gel Solution Composition | |
|---|---|
| Ingredients | Wt. % |
| Water, deionized | qs |
| Lightly crosslinked PVP | 0.50 |
| Terpolymer of Ex. 2 | 4 |
| Glycerine | 50 |
| GERMALL ® II (Sutton) | 0.30 |

Procedure
1. Prepare a mixture of lightly crosslinked PVP in an aqueous solution of the terpolymer with stirring for 10 minutes at 40–500C. until thickening occurs.
2. Add glycerine slowly over 10 minutes with stirring. Stir until uniform gel is obtained.
3. Add remaining ingredients, mixing thoroughly after each addition.

EXAMPLE 13'

| Hydroalcoholic Gel | |
|---|---|
| Ingredients | Wt. % |
| Ethanol | 70.0 |
| Water, deionized | qs |
| Lactic acid | 15.0 |
| Glycerine | 3.0 |
| Lightly crosslinked PVP | 0.8 |
| Terpolymer of Ex. 2 | 3.5 |
| Additives | qs |

Procedure
1. Prepare hydrogel by adding lightly crosslinked PVP in ethanol, water, glycerine, lactic acid, then heat to 400–500C. in suitable enclosed vessel with stirring for 15 minutes.
2. Start cooling.
3. Add remaining ingredients with stirring. Mix thoroughly after each addition, until uniform gel is obtained.

EXAMPLE 14'

| Spray Gel | |
|---|---|
| Ingredients | W. % |
| Ethanol | 60.00 |
| Water, deionized | qs |
| Lightly crosslinked PVP | 0.4 |
| P(VP-VA) S-60 | 0.6 |
| Terpolymer of Ex. 2 | 2 |
| Additives | qs |
| Neutralize to pH 4.0 | qs |

Procedure
1. Prepare a spray gel by adding lightly crosslinked PVP in water, ethanol, composition of Ex. 1 and P(VP-VA) S-60 for 15 minutes, then heat to 450C.–600C. in suitable enclosed vessel with stirring for 30 minutes.
2. Start cooling.
3. Add remaining ingredients with stirring. Mix thoroughly after each addition, until uniform. Suggested Pump: —Calmar Mistette, Mark II, 0.20 ml/stroke, yellow orifice (high viscosity).

EXAMPLE 15'

The composition of the invention is particularly suitable for use as the active ingredient in a kerototic plug remover, or skin pore strip, such as is described in detail in U.S. Pat. No. 5,512,277. Such strips comprise the composition applied to a backing which Way be a woven or non-woven material, suitably paper or plastic. Then the solution is dried to form the pore strip. Before use, the strip is moistened and applied to the part of the skin to be rejuvenated. After further drying, the strip is peeled off with the unsightly skin pore.

While the invention has been described with particular reference to certain embodiments thereof, it will be understood that many alterations and modifications may be made which are considered within the scope of this invention and which will become apparent from the foregoing disclosure.

What is claimed is:

1. A cosmetic composition for rejuvenating the appearance of skin with substantially no skin irritation, in the form of a lotion, creme, solution or gel, on a carrier, consisting essentially of an aqueous, alcoholic or aqueous-alcoholic solution of 0.5 to 50 wt. % of a copolymer having a carboxylic acid functionality which is a terpolymer of methyl vinyl ether/maleic acid/isobutylene, said composition having a pH of 1.5 to 5, wherein the carrier comprises wovens and non-wovens.

2. A cosmetic composition according to claim 1 in which said pH is about 2 to about 4.5.

3. A cosmetic composition according to claim 1 which includes about 0.75 to about 25 wt. % of the terpolymer.

4. The composition of claim 1 wherein the composition optionally contains between about 0.1 and about 10 wt. % of at least one of the adjuvants selected from the group consisting of an emollient, a moisturizer, a thickener, an emulsifier, a neutralizer, a non-toxic coloring agent, a UV absorber, a preservative and a gelling agent.

5. A cosmetic composition according to claim 1 which contains 20–95 wt. % of water.

6. A cosmetic composition for rejuvenating the appearance of skin with substantially no skin irritation, having excellent skin substantivity, in the form of a lotion, creme, solution or gel, or on a carrier consisting essentially of an aqueous, alcoholic or aqueous-alcoholic solution of 0.5 to 50 wt. % of solvent-free, fine white powders of an alternating terpolymer of maleic anhydride, a $C_1$–$C_4$ alkyl vinyl ether and isobutylene having a molecular structure $(A-B)_n$, where A is maleic anhydride and B is alkyl vinyl ether or isobutylene, and having a mole ratio of maleic anhydride to alkyl vinyl ether to isobutylene of 0.50:0.45–0.25:0.05–0.25, which has a weight average molecular weight of at least about 1,500,000, as measured by GPC in water (pH 9), and a specific viscosity of $\geq 6$, as measured on 1% solutions in DMF (dimethylformamide), said composition having a pH of 1.5 to 5, which is applied onto a carrier including wovens and non-wovens.

7. A cosmetic composition according to claim 6 in which the terpolymer has about 10–15 mole % isobutylene.

8. A cosmetic composition according to claim 6 in which the pH is about 2 to about 4.5.

9. A cosmetic composition according to claim 6 which includes about 0.75–25 wt. % of said terpolymer.

10. A cosmetic composition according to claims 1 or 6 wherein the carrier is paper or plastic.

* * * * *